(12) United States Patent
Emslie et al.

(10) Patent No.: US 6,361,765 B1
(45) Date of Patent: Mar. 26, 2002

(54) COSMETIC COMPOSITIONS

(75) Inventors: Bruce Steven Emslie, Bebington;
Laura Dimitrova Stoimenof, London;
Graham Andrew Turner, Bebington,
all of (GB)

(73) Assignee: Unilever Home & Personal Care USA, division of Conopco, Inc., Chicago, IL (US)

( * ) Notice: Subject to any disclaimer, the term of this patent is extended or adjusted under 35 U.S.C. 154(b) by 0 days.

(21) Appl. No.: 09/586,589

(22) Filed: Jun. 2, 2000

(30) Foreign Application Priority Data

Jun. 3, 1999 (GB) .............................. 9912924
May 8, 2000 (GB) .............................. 0011084

(51) Int. Cl.[7] .................................. A61K 7/32
(52) U.S. Cl. .................. 424/65; 424/401; 424/66; 424/67; 424/68
(58) Field of Search .............................. 424/401, 65–68

(56) References Cited

U.S. PATENT DOCUMENTS

| | | | |
|---|---|---|---|
| 3,792,068 A | 2/1974 | Luedders et al. | 260/429.3 |
| 4,265,878 A | 5/1981 | Keil | 424/68 |
| 4,704,271 A | 11/1987 | Hourihan et al. | 424/66 |
| 4,724,139 A | 2/1988 | Palinczar | 424/66 |
| 4,948,584 A | 8/1990 | Brand | 424/401 |
| 5,102,656 A | 4/1992 | Kasat | 424/66 |
| 5,162,378 A | 11/1992 | Guthauser | 514/785 |
| 5,176,902 A | 1/1993 | Castro et al. | 424/63 |
| 5,281,413 A | 1/1994 | Abrutyn et al. | 424/68 |
| 5,292,530 A | 3/1994 | McCrea et al. | 424/66 |
| 5,486,347 A | 1/1996 | Callaghan et al. | 423/623 |
| 5,885,559 A | 3/1999 | Lee et al. | 424/65 |
| 6,086,887 A | * 7/2000 | Parrott | 424/195.1 |

FOREIGN PATENT DOCUMENTS

| | | |
|---|---|---|
| DE | 196 43 238 | 4/1998 |
| EP | 0061701 | 10/1982 |
| EP | 0252463 | 1/1988 |
| EP | 0281288 | 9/1988 |
| EP | 0295071 | 12/1988 |
| EP | 0 295 071 A2 * | 12/1988 |
| EP | 0319062 | 6/1989 |
| EP | 0291334 | 9/1993 |
| GB | 2299506 | 10/1996 |
| WO | 98/09609 | 3/1998 |
| WO | 98/09712 | 3/1998 |
| WO | 98/17238 | 4/1998 |
| WO | 98/27939 | 7/1998 |

OTHER PUBLICATIONS

Search Report under Section 17(5) Application No. GB 9912924.9 dated Sep. 30, 1999.
International Search Report Application No. PCT/EP 00/05106 mailed Oct. 13, 2000.

* cited by examiner

*Primary Examiner*—Jose' G. Dees
*Assistant Examiner*—Konata M. George
(74) *Attorney, Agent, or Firm*—Kevin J. Stein

(57) ABSTRACT

Antiperspirant compositions herein comprise an antiperspirant active, together with a carrier and a structurant for the carrier which comprises an organic wax having a melting point of from 40 to 90° C. of which at least 60% of the weight of the wax is provided by at least one aliphatic ester satisfying the formula:

$$CH_3-(CH_2)_n-CO-(CH_2)_m-CH_3$$

in which n is from 9 to 39 and m is from 0 to 35 to form a solid or a soft solid. The compositions can be anhydrous, in the form of a suspension of antiperspirant active, or can comprise aqueous emulsions.

The formulations structured by the selected waxes provide lower visible deposits on topical application compared with conventional wax-structured formulations and the waxes are effective at structuring/thickening at a proportion below that in conventional wax-structured formulations.

It is especially desirable to employ emulsion formulations comprising a continuous phase which comprises from 10 to 35% volatile silicone oil, and from 5 to 15% non-volatile hydrophobic oil, from 40 to 75% of ta disperse aqueous phase which contains from 1 to 35% of an antiperspirant or deodorant active, from 7 to 25% of a wax structurant, from 0.1 to 10% of an emulsifier, and preferably contains up to 5% insoluble particulate materials, % s being by weight based on the composition.

35 Claims, No Drawings

COSMETIC COMPOSITIONS

FIELD OF THE INVENTION

The present invention relates to cosmetic compositions containing a thickened or structured liquid and in particular to such compositions containing an antiperspirant and/or deodorant active.

BACKGROUND AND PRIOR ART

Topically applied antiperspirant compositions are in widespread use throughout much of the world, in order to enable their users to avoid or minimise visible wet patches on their skin, especially in axillary regions. Antiperspirant formulations have been applied using a range of different applicators, including aerosols, roll-ons, pump sprays, sticks and mushroom applicators, in accordance with the individual preferences of consumers. In some parts of the world, sticks are especially popular. The term stick traditionally indicates a bar of solid material which was usually housed within a dispensing container and which retains its integrity whilst being applied, ie a firm stick. When a portion of a firm stick is drawn across the skin surface, a film of the stick composition is transferred onto the skin surface. Although the stick has the appearance of a solid article, the material forming the stick usually comprises a structured liquid phase such that a film of the material is readily transferred onto another surface upon contact under pressure.

More recently, the term has been applied to soft solids, which have an apparent solid form during storage, but which flow under mild pressure or shear, so that in use they can be extruded through an aperture or apertures onto a dispensing surface. Soft solids retain their shape for at least 30 seconds after extrusion under such non-shear/low stress conditions from a container, but if subjected to high shear or stress, their structure is destroyed and no more than a minor fraction of the structure can be reformed within a period of about 24 hours when the shear/stress is removed.

There are typically three classes of antiperspirant sticks, namely suspension sticks, emulsion sticks and solution sticks. Suspension sticks contain a particulate antiperspirant active material suspended in a structured carrier. Emulsion sticks normally comprise an emulsion of an oil phase and a hydrophilic phase containing the antiperspirant active in solution, the continuous phase being structured. In some emulsion sticks, the continuous phase is an oil phase. In solution sticks, the antiperspirant is typically dissolved in the liquid carrier phase which is structured. The liquid phase in a solution stick can comprise water and/or a water-miscible organic solvent. The three categories can be applied to sticks of both firm and soft solids compositions.

Conventionally, many sticks have been structured using naturally occurring or synthetic waxes, of which typical examples include stearyl alcohol, and hydrocarbon waxes or silicone waxes. waxes are widely available, and by suitable selection of the waxes themselves and their concentrations in the formulation can effectively obtain either a soft solid or a firm solid. Thus, for example, wax-structured sticks are described in an article in Cosmetics and Toiletries, 1990, vol. 105, p75–78. Wax-thickened creams are described in U.S. Pat. No. 5,102,656 (Kasat.)

However, and although the disadvantage is not mentioned in either of the above-identified references, it has been observed that wax structured compositions tend to leave visible white deposits on application to human skin, and the deposits can also be transferred onto clothing by physical contact with the skin. A significant, and possibly growing, proportion of consumers of antiperspirants have indicated displeasure at visible deposits. Accordingly, the antiperspirant industry, including the instant inventors, is devoting considerable time and resources to finding means to ameliorate or overcome the customer perception of white deposits.

Amongst the class of naturally occurring waxes which have been used or contemplated for use in thickening or structuring an oily liquid phase of an antiperspirant or deodorant composition, animal-derived waxes include beeswax, and vegetable-derived waxes include candelilla wax and carnauba wax. Each of these waxes comprises in general terms a mixture of a) esters, often including an alkyl moiety of at least 8 carbons length derivable from a fatty acid or fatty alcohol, and/or an aromatic hydrocarbon moiety, b) non-esterified fatty acids, c) non-esterified fatty alcohols, d) non-gaseous hydrocarbons and e) resins. The proportions of the wax constituents varies depending on the particular wax selected, and to a lesser extent on their geographical location where they are produced and the time of year.

Various disadvantages have been attributed to the incorporation of naturally occurring waxes, including in particular beeswaxes, such as the disadvantage of variation in properties of the waxes arising from their natural variation in constitution and also the disadvantage arising from the presence of the non-esterified acids and/or alcohols in the wax mixtures. Accordingly, in a number of disclosures, some waxes have been subjected to chemical processes to increase their esters content, prior to their incorporation in a cosmetic formulation.

For example, in U.S. Pat. No. 5,176,902, a coloured cosmetic stick is obtained by incorporating a wax which had been esterified with a C1–60 mono or polyhydric alcohol to convert all naturally present C12–60 fatty acids into their respective esters. In J Kokai 58–092605 there is described the production of a modified beeswax in which free acids are esterified. The product was stated to have excellent pigment dispersibility, e.g. in a massage cream. In EPA-319062 and U.S. Pat. No. 4,948,584, Koster Keunen describe a process for modifying beeswax by removing free acids. The resultant product has self-emulsifying characteristics. None of those publications mention the visible white residue of structured or thickened antiperspirant or deodorant compositions and in consequence give no teaching on how to ameliorate or solve the problem.

However, the principle reason for incorporating a wax in a formulation is often to structure or thicken a carrier fluid forming a firm or soft solid. It is advantageous to identify waxes which have a superior ability to structure or thicken a carrier fluid. For example, only a smaller proportion of the wax is needed to achieve a desired extent of thickening or structuring, thereby increasing the options on the producer of cosmetic compositions to vary the remaining constituents. Moreover, the inventors recognised that waxes can be now implicated in at least contributing to the visibility of deposits on skin, and so they concluded that visible deposits may be observable to a lesser extent if less wax were needed.

Cosmetic compositions thickened or structured using polysiliconyl modified beeswaxes have been described in WO 98/09609 and using hexanediol-behenyl beeswaxes in WO 98/09712. However, in the course of their present investigations, the present inventors have found that the capability of derivatives of beeswax to thicken or structure an antiperspirant or deodorant carrier fluid varies, depending on the nature of the modification. Thus, for example, polysiliconyl-modified beeswaxes and fatty acid esterification of free fatty acids in beeswaxes (as in the production of hexanediol-behenyl beeswaxes) have both been observed to produce materials having a relatively poor structuring capability. Consequently, a pre-treatment of beeswaxes does not necessarily result in the modified beeswax having an effective structuring capability.

One class of stick which has been contemplated for antiperspirant or deodorant application comprises an emulsion stick. Such sticks comprise a continuous phase in which droplets of a second liquid phase are dispersed, normally referred to as a disperse phase. The continuous phase is one of hydrophobic or aqueous, and the disperse phase constitutes the other. The antiperspirant or deodorant active is conveniently incorporated within the aqueous phase. The hydrophobic phase can be structured by incorporation of wax structurants, these being materials which typically are solid at ambient temperatures, but which melt or dissolve or disperse into the oils constituting the hydrophobic phase at elevated temperatures, for example selected between 60 and 120° C., depending on the choice of oil and wax. When the mixture of wax structurant and oil cools to below its setting temperature, the oil phase solidifies.

When formulating emulsion sticks, there are a number of factors to be taken into account. Some of the factors are antagonistic. One of the first and very important factor relates to the respective proportions of the two phases. The antiperspirant salts have finite solubility in the aqueous phase, so that antiperspirant efficacy potentially increases as the proportion of the aqueous phase increases. However, any increase in the proportion of aqueous phase in the formulation results in a corresponding decrease in the space available to the hydrophobic phase. In conjunction with the choice of its constituent oil or oils, this affects the ability of the hydrophobic phase to provide a strong supporting continuous phase, and hence the strength and integrity of the stick. Moreover, it affects the ability of that phase to contain beneficial hydrophobic constituents.

Waxes have been commonly used or proposed for use in structuring anhydrous formulations, in which a particulate antiperspirant is suspended in an oil phase, but much less attention has been given to their use to structure emulsion sticks.

The market for underarm products is constantly evolving as consumers' tastes and lifestyles change. One attribute of underarm formulations to which consumers have paid considerable attention in recent years is the extent to which the formulation is visible on the skin, either shortly after application or subsequently throughout the following day. This is commonly referred to as visible deposits. Waxes and antiperspirant salts can give rise to visible deposits on human skin, so that in line with current consumer preferences, it would be desirable to be able to reduce or ideally eliminate them. A related attribute relates to the visibility of the formulation on any clothing, either occurring in the course of its application to the skin or by subsequent transfer by contact of the skin with the clothing. Likewise, it would be desirable to reduce or ideally eliminate visible deposits on clothing.

Some oils are effective carriers for distributing antiperspirant or deodorant actives on the skin, but have little effect on visible deposits. Various other oils can ameliorate the appearance of visible deposits, but the space available for such oils in emulsions is constrained by the proportion occupied by the aqueous phase.

The effect of the oils on the ease with which a firm emulsion stick can be formulated has been mentioned herein before. A further factor relates to the variation in sensory attribute of emulsion sticks made using different oils. Thus, for example, the formulation have a high drag on passage across the skin or they can show a filmy deposit on the skin. They can appear to be sticky when in the dispensing container or on application to the skin, or they feel greasy.

The prior art contains various publications disclosing sticks containing an aqueous component. Thus, for example U.S. Pat. No. 4,265,878 exemplifies a formulation containing substantially no non-volatile oil. The formulation exhibits high visible deposits. U.S. Pat. No. 5,162,378 discloses emulsions containing an aqueous phase, but without a non-volatile oil. Like '878, it provides no teaching on the problems associated with formulations containing non-volatile oils and how to solve them. U.S. Pat. No. 4,704,271 discloses formulations containing a high proportion of disperse aqueous phase, a continuous phase containing a low proportion of non-volatile oil and a high ratio of volatile to non-volatile oils, structured with stearyl alcohol. This formulation has an intrinsically high level of visible deposits from its active and structurant which is reduced to only a limited extent.

WO 98/17238 exemplifies emulsion formulations containing non-volatile oils that are free from volatile silicones. Consequently, it is silent as to the constraints relating to formulations which desire to contain both such constituents and the benefits from containing both of them in selected proportions.

EP-A-0291334 circumvents the use of waxes by employing a liquid crystal phase to structure the product. Accordingly, it provides no teaching concerning the provision of wax-structured emulsions containing both a volatile silicone and a non-volatile oil.

EP-A-0281288 exemplifies an antiperspirant formulation in which an oil phase containing only a small proportion of a non-volatile oil is structured with stearyl alcohol. Such a formulation exhibits a high drag and indeed also has a relatively high visible deposit. Accordingly, it does not provide teaching on how to address such issues. EP-A-0295071 discloses emulsion sticks employing a disperse phase based on a polyhydric alcohol, which can also contain a minor proportion of water. Propylene glycol is exemplified in a 4:1 weight ratio to water in the disperse phase. Sticks which are based on propylene glycol as the principal lipophobic constituent typically exhibit stickiness.

OBJECTS OF THE PRESENT INVENTION

It is an object of the present invention to provide a thickened or structured antiperspirant composition which ameliorates or overcomes simultaneously the disadvantage of visible deposits whilst employing a wax having superior structuring capability.

It is a further object of certain preferred embodiments to provide an emulsion stick formulated employing a wax having superior structuring capability and exhibiting a desirable combination of sensory attributes, stick integrity and reduction of visible deposits.

SUMMARY OF THE PRESENT INVENTION

According to a first aspect of the present invention, there is provided an antiperspirant composition comprising an antiperspirant active, a liquid carrier and a structurant or thickener for the carrier characterised in that the structurant or thickener comprises an organic wax having a melting point of from 40 to 90° C. of which at least 60% of the weight of the wax is provided by at least one aliphatic ester satisfying the formula:

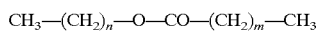
$$CH_3-(CH_2)_n-O-CO-(CH_2)_m-CH_3$$

in which n is from 9 to 39 and m is from 0 to 35.

By the employment of a wax meeting the criteria of selection of the chemical constitution of the specified constituent and its employment as the greater part of the wax, the goal can be attained of employing a wax which ameliorates the disadvantage of visible deposits whilst offering effective structuring capability.

DETAILED DESCRIPTION OF THE INVENTION

In compositions according to the present invention, an essential constituent of the thickening/structuring wax is an ester in accordance with the general formula:

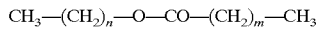
$$CH_3-(CH_2)_n-O-CO-(CH_2)_m-CH_3$$

in which n is from 9 to 39 and m is from 0 to 35.

The selected ester, or, more normally, mixtures of esters satisfying the general formula, can comprise, if desired, up to 100% of the wax, with the remainder of the wax being satisfied by beeswax or one or more constituents thereof or by a secondary waxy structurant or thickener. In many embodiments, the proportion of the selected ester is at least 70% by weight, preferably at least 80% by weight and most desirably at least 90% by weight of the wax.

It is desirable that the wax employed herein comprises at most no more than a small proportion of free carboxylic acid and hydrocarbons. Preferably, the wax contains no more than about 4% and particularly no more than about 2% by weight non-esterified carboxylic acid. It is highly desirable that the content of hydrocarbons in the wax is less, and indeed much less than in a conventional beeswax, particularly is less than 5% by weight and especially from 0 to 2% by weight of the wax.

Within the general formula for the ester, a range of preferred esters comprises those in which n is selected within the range of 14 to 24 and especially 16–20 together with m being selected in the range of 14 to 24 and especially 16 to 20. In second range of preferred esters within the general formula, n is selected in the range of 18 to 38 and m is either 0 or 1. It will be understood that mixtures of esters within each preferred range or mixtures of one preferred range of esters with the other can be employed. Convenient mixtures include a mixture of a wax comprising esters of n=14 to 20 and m=14 to 20 with a wax comprising esters of n=16 to 20 and m=14 to 20 or preferably 16 to 20.

Esters in accordance with the formula given herein can be obtained by a conventional esterification reaction carried under conventional reaction conditions described in the literature for reaction between an alcohol having the chain length appropriate to provide "n" in the ranges specified above and a carboxylic acid having a chain length appropriate to yield "m" in the ranges specified above.

The wax is employed herein normally within the range of from 2 to 25% by weight, based on the composition. Where a firm solid composition is desired, the wax proportion is normally at least 5% by weight, and is often selected in the range of from 6 to 15% by weight of the composition. Where a soft solid composition is desired, the wax proportion is normally below 5%, and particularly from 2 to 4% by weight. It will be understood that when the wax is employed at or near the boundary, i.e. in the region of 5%, the resultant material may be a soft solid or a firm solid having relatively low hardness in a standard sphere indentation test.

An essential constituent of antiperspirant compositions is an antiperspirant active. Antiperspirant actives, are preferably incorporated in an amount of from 0.5–60%, particularly from 5 to 30 or 40% and especially from 10 to 30 or 35%.

Antiperspirant actives for use herein are often selected from astringent active salts, including in particular aluminium salts, zirconium salts and mixed aluminium-zirconium salts, including for each both inorganic salts and organic salts and complexes. Preferred astringent salts include aluminium, zirconium and aluminium-zirconium halides and halohydrate salts, such as chlorohydrates.

Preferred aluminium salts include aluminium halohydrates having the general formula $Al_2(OH)_xQ_y \cdot wH_2O$ in which Q represents chlorine, bromine or iodine, x is from 2 to 5 and x+y=6, x and y being either integers or non-integers and w represents a variable amount of hydration, which may be zero. Some especially preferred halohydrate salts comprise activated aluminium chlorohydrates such as those described in EP-A-6739 (Unilever NV et al), the contents of which specification is incorporated herein by reference. Activated salts retain their enhanced activity and are advantageously employed in substantially anhydrous formulations, i.e. formulations which do not contain a distinct aqueous phase. Some activated salts can also retain their enhanced activity in hydrous formulations too.

A range of zirconium salts which can be employed desirably in antiperspirant compositions herein is represented by the following empirical general formula: $ZrO(OH)_{2n-nz}B_z \cdot wH_2O$ in which z is an integer or non-integer in the range of from 0.9 to 2.0, n is the valency of B, 2−nZ is at least 0, B is selected from the group consisting of halides, including chloride, sulphamate, sulphate and mixtures thereof and w represents a variable amount of hydration, which may be zero. In preferred zirconium salts B represents chloride and z lies in the range of from 1.5 to 1.87. In practice, such zirconium salts are usually not employed by themselves, but as a component of a combined aluminium and zirconium-based antiperspirant, the aluminium component normally being selected in accordance with the above-mentioned formula for halohydrates. Especially desirable salts comprise mixed aluminium-zirconium chlorohydrates, optionally activated.

It will be recognised that the above-identified formulae for aluminium and zirconium salts are empirical and encompass compounds having co-ordinated and/or bound water in various quantities as well as polymeric species and mixtures and complexes. In particular, zirconium hydroxy salts often represent a range of salts having various amounts of the hydroxy group.

Antiperspirant complexes based on the above-mentioned astringent aluminium, zirconium and aluminium/zirconium salts can desirably be employed in the present invention. Preferably, aluminium halohydrate and/or zirconium chlorohydrate materials are complexed. The complex often employs a carboxylic acid or carboxylate group, and advantageously an aminoacid. Examples of suitable aminoacids include dl-tryptophane, dl-β-phenylaniline, dl-valine, dl-methionine and β-aniline, and preferably glycine which satisfies the formula $CH_3(NH_2)CO_2H$.

It is highly desirable to employ complexes of a combination of aluminium halohydrates and zirconium chlorohydrates together with aminoacids such as glycine, such as those disclosed in U.S. Pat. No. 3,792,068 (Luedders et al). Certain of those Al/Zr complexes are commonly called ZAG in the literature. ZAG actives generally contain aluminium, zirconium and chloride with an Al/Zr ratio in the range of 2 to 10, especially 2 to 6, a ratio of (Al-Zr)/Cl in the range of 2.1 to 0.9 and a variable amount of an amino acid, particularly glycine. Actives of this preferred type are available from Westwood, Summit and Reheis.

In some formulations, it is particularly preferably to employ activated ZAG complexes which can be produced by the process disclosed in U.S. Pat. No. 5,486,347 (Callaghan et al).

Other actives which can be utilised comprise aluminium lactates, borate cross-linked aluminium salts, and astringent titanium salts, for example those described in GB 2299506A. Yet other actives includes chlorlinergenics, antihistamines and antiandrenerics.

The proportion of solid antiperspirant salt in the composition normally includes the weight of any water of hydration and any complexing agent that may also be present. However, when the antiperspirant salt is dissolved in aqueous solution, its weight excludes any water present.

In some embodiments of the present invention, the antiperspirant salts is employed herein in particulate form, and particularly in compositions which do not comprise an aqueous or hydrophilic phase. Such compositions are conveniently referred to as anhydrous or substantially anhydrous. The particle size of antiperspirant salts in such compositions often falls within the range of 1 to 200 μm with a mean particle sizes often from 3 to 20 μm, such as when conventional barrels are filled using conventional cast processes. Both larger and smaller mean particle sizes can also be contemplated such as from 20 to 50 μm or 0.1 to 3 μm.

In other embodiments, the antiperspirant active can be employed in solution form, for example where the composition comprises a polar phase, normally comprising water and/or a water-miscible solvent. In such embodiments, the concentration of antiperspirant active in solution (in the disperse polar phase) is often in the range of from 3 to 60%, based on solely the polar phase, particularly from 10% or 20% up to 55% or 60% of that phase.

The third essential constituent of the composition is a liquid carrier, often in a proportion of from 30 to 95% of the composition, and particularly from 40 to 90%.

The carrier that is incorporated in compositions herein comprises one or more materials that is liquid at which the composition is used and can be gelled or otherwise structured by the structurant to provide a firm or extrudable solid at that use temperature, which conventionally is residential ambient, which is usually below 40° C. and in many instances below 30° C. and often at least 15° C. The carrier can be hydrophobic or a mixture of both hydrophobic and hydrophilic, the latter normally being in the form of an emulsion. It is particularly desirable that the carrier herein contains sufficient hydrophobic material to produce a continuous phase in which a discontinuous hydrophilic phase or particulate phase can be dispersed. The twin gellant system of the present invention is suited especially to gelling a hydrophobic medium and can also structure a dispersed oil phase, should that be present.

The hydrophobic carrier liquid may have some volatility or contain volatile constituents but generally its vapour pressure will be less than 4 kPa at 25° C., so that it can be described as an oil or mixture of oils. More specifically, it is desirable that at least 80% by weight of the hydrophobic carrier liquid should consist of materials having a vapour pressure not above 4 kPa at 25° C.

One class of carriers that is particularly desirable herein is hydrophobic and comprises liquid silicones, in order to promote good sensory properties at the time of use of the formulation. Preferably at least a major fraction of the silicone carrier is constituted by at least one volatile polyorganosiloxane, i.e. liquid materials having a measurable vapour pressure at ambient conditions (about 20 to 25° C.). Typically the vapour pressure of volatile silicones lies in the range of from 1 or 10 Pa to 2 kPa at 25° C. Volatile polyorganosiloxanes can be linear or cyclic or mixtures thereof. Preferred cyclic siloxanes include polydimethylsiloxanes and particularly those containing from 3 to 9 silicon atoms and preferably not more than 7 silicon atoms and most preferably from 4 to 6 silicon atoms, otherwise often referred to as cyclomethicones. Preferred linear siloxanes include polydimethylsiloxanes containing from 3 to 9 silicon atoms. The volatile siloxanes normally by themselves exhibit viscosities of below $1\times10^{-5}$ m$^2$/sec (10 centistokes), and particularly above $1\times10^{-7}$ m$^2$/sec (0.1 centistokes), the linear siloxanes normally exhibiting a viscosity of below $5\times10^{-6}$ m$^2$/sec (5 centistokes). The volatile silicones can also comprise branched linear or cyclic siloxanes such as the aforementioned linear or cyclic siloxanes substituted by one or more pendant —O—Si(CH$_3$)$_3$ groups. Examples of commercially available silicone oils include oils having grade designations 344, 345 244, 245 and 246, (from Dow Corning Corporation) Silicone 7207 and Silicone 7158 (from Union Carbide Corporation) and SF1202 (from General Electric [US]). Volatile silicones are often present in the composition in a proportion of up to 80% particularly from 10 to 70% and in a number of instances from 20 to 60%.

The hydrophobic carrier employed in compositions herein can alternatively or additionally comprise non-volatile silicone oils, which include polyalkyl siloxanes, polyalkylaryl siloxanes and polyethersiloxane copolymers. These can suitably be selected from dimethicone and dimethicone copolyols. Commercially available non-volatile silicone oils include Dow Corning 556 and Dow Corning 200 series having a viscosity of at least 50 centistokes. Non-volatile silicones are often present in not more than about 30% by weight of the composition, and preferably from 1 to 15% by weight. In many instances, when a non-volatile silicone oil is present, its weight ratio to volatile silicone oil is chosen in the range of from 1:3 to 1:40.

Silicon-free hydrophobic organic carriers can be incorporated in the invention compositions in addition to or instead of liquid silicones, i.e. from 0 to 100% of the hydrophobic carrier liquids. Such silicon-free hydrophobic organic carrier materials can include liquid aliphatic hydrocarbons such as mineral oils or hydrogenated polyisobutene, often selected to exhibit a low viscosity. Further examples of liquid hydrocarbons comprise polydecene and isoparaffins containing at least 10 carbon atoms and often in the region of up to 30 carbons.

Other suitable hydrophobic carriers comprise liquid aliphatic or aromatic esters, as a fraction of the water-immiscible carrier, desirably not more than 20% and in many instances less than 10% of the weight of the water-immiscible carrier.

Suitable aliphatic esters contains at least one long chain alkyl group, such as esters derivable from $C_1$–$C_{20}$ alkanols esterified with a $C_8$ to $C_{22}$ alkanoic acid or $C_6$ to $C_{10}$ alkanedioic acid. The alkanol and acid moieties or mixtures thereof are preferably selected such that they have a melting point of below 20° C. Suitable esters include isopropyl myristate, lauryl myristate, isopropyl palmitate, diisopropyl sebacate and diisopropyl adipate.

Suitable liquid aromatic esters, preferably have a melting point of below 20° C., including fatty alkyl benzoates. Examples of such esters include suitable C8 to C18 alkyl benzoates or mixtures thereof.

Further instances of suitable hydrophobic carriers comprise liquid aliphatic ethers derivable from at least one fatty alcohol, such as myristyl ether derivatives e.g. PPG-3 myristyl ether or lower alkyl ethers of polyglycols such as PPG-14 butyl ether. The proportion of ether in a formulation according to the present invention is often selected in the range of from 0 to 40% w/w and in some formulations particularly from 1 to 30% w/w.

Yet other suitable hydrophobic carriers comprise liquid aliphatic alcohols containing at least 10 carbon atoms which are liquid at 20° C. Examples of such alcohols include branched chain alcohols such as ethylhexyl alcohol, octyldodecanol and isostearyl alcohol. The proportion of the alcohol in a formulation according to the present invention is often selected in the range of from 0 to 40% w/w and particularly from 1 to 30% w/w.

The total proportion of non-silicone hydrophobic carrier (s) is often chosen in the range of from 0 to 80% and particularly from 5 to 70% by weight of the carrier. Mixtures of hydrophobic non-silicone organic carriers can be employed. If oxygen-containing silicon-free hydrophobic organic liquids are employed, they desirably constitute not more than 70% by weight of the hydrophobic carrier. Lower proportions of the hydrophobic phase, ranging up to for example 20, 30 or 35% in total by weight are more likely.

Mixtures of silicone and non-silicone carriers can suitably be employed herein, in any weight ratio, and in a number of tested embodiments the ratio lies in the range of from 20:1 to 1:20.

The carrier or mixture of carrier employed in the present invention can be and in many effective compositions is anhydrous, i.e. contain no free water, by employing solely one or more hydrophobic carriers. Alternatively, if desired, the composition can comprise a hydrophilic carrier, such as in particular water and/or a water-miscible organic solvent such as an alcoholic water-miscible solvent, in addition to a hydrophobic carrier, such as those indicated hereinbefore. Compositions containing both a hydrophobic and a hydrophilic carrier normally have one of them as a disperse phase. Formulations containing a disperse phase in practice would often further comprise an emulsifying surfactant, such as an anionic, cationic, zwitterionic and/or nonionic surfactant.

In emulsions herein, the disperse phase, including any material dissolved therein, normally constitutes from 5 to 80% of the weight of the composition and in many embodiments up to 65% by weight and in such or other embodiments preferably at least 25% by weight by weight. The continuous phase containing structurant therefor provides the weight balance of the composition, such as from 20 to 95% by weight. The emulsions herein normally comprises a water in oil emulsion, i.e. the disperse phase is the hydrophylic phase . Where an emulsion is employed, it can be convenient to prepare an emulsion as a separate step before it is mixed with the remaining constituents of the composition.

The emulsion in many instances incorporates one or more emulsifiers, which often are non-ionic. The proportion of emulsifier or emulsifier system, i.e. combination of emulsifiers, in the emulsion is often selected in the range of from 0.1 to 10% w/w, and in many instances from 0.25 to 5% w/w. Most preferred is an amount of from 0.1 or 0.25% up to 3% w/w. It is desirable to employ an emulsifier or emulsifier system providing an overall HLB value in a range of from 2 to 10 and preferably from 3 to 8.

It may be convenient to employ an emulsifier system employing in combination an emulsifier having an HLB value above a desired overall value and one having an HLB value below the desired value. By employing the two emulsifiers together in appropriate ratios, it is readily feasible to attain a weighted average HLB value that promotes the formation of an emulsion.

Many suitable emulsifiers are nonionic ester or ether emulsifiers comprising a polyoxyalkylene moiety, especially a polyoxyethylene moiety, often containing from about 2 to 80, and especially 5 to 60 oxyethylene units, and/or contain a polyhydroxy compound such as glycerol or sorbitol or other alditols as hydrophilic moiety. The hydrophilic moiety can contain polyoxypropylene. The emulsifiers additionally contain a hydrophobic alkyl, alkenyl or aralkyl moiety, normally containing from about 8 to 50 carbons and particularly from 10 to 30 carbons. The hydrophobic moiety can be either linear or branched and is often saturated, though it can be unsaturated, and is optionally fluorinated. The hydrophobic moiety can comprise a mixture of chain lengths, for example those deriving from tallow, lard, palm oil sunflower seed oil or soya bean oil. Such non-ionic surfactants can also be derived from a polyhydroxy compound such as glycerol or sorbitol or other alditols. Examples of emulsifiers include ceteareth-10 to –25, ceteth-10-25, steareth-10-25, and PEG-15-25 stearate or distearate. Other suitable examples include C10–C20 fatty acid mono, di or tri-glycerides. Further examples include C18–C22 fatty alcohol ethers of polyethylene oxides (8 to 12 EO). The co-emulsifiers, which typically have a low HLB value, and often of from 2 to often comprise mono or possibly fatty acid diesters of polyhydric alcohols such as glycerol, sorbitol, erythritol or trimethylolpropane. The fatty moiety is often from C14 to C22 and is saturated in many instances, including cetyl, stearyl arachidyl and behenyl. Examples include monoglycerides of palmitic or stearic acid, sorbitol mono or diesters of myristic palmitic or stearic acid, and trimethylolpropane monoesters of stearic acid.

A particularly desirable class of emulsifiers comprises dimethicone copolymers, namely polyoxyalkylene modified dimethylpolysiloxanes. The polyoxyalkylene group is often a polyoxyethylene (POE) or polyoxypropylene (POP) or a copolymer of POE and POP. The copolymers often terminate in C1 to C12 alkyl groups.

Suitable emulsifiers are widely available under many tradenames including Abil™, Arlacel™, Brij™, Cremophor™, Dehydrol™, Emerest™, Lameform™, Quest PGPH™, Pluronic™, Prosorine™, Span™, Tween™, SF 1228, DC3225C and Q2-5200.

The hydrophilic carrier normally comprises water and can comprise one or more water soluble or water miscible liquids in addition to or replacement for water. The proportion of water in an emulsion according to the present invention is often selected in the range of up to 60%, and particularly from 5 to 40%. Some of the water may be introduced as a solvent for the antiperspirant active.

One class of water soluble or water-miscible solvents comprises short chain monohydric alcohols, e.g. C1 to C4 and especially ethanol or isopropanol, which can impart a deodorising capability to the formulation. A further class of hydrophilic liquids comprises di or polyols, preferably having a melting point of below 40° C., or which are water miscible. Examples of di or polyols include glycol, 1,2 propylene glycol, 1,3 butylene glycol, hexylene glycol, diethylene glycol, dipropylene glycol 2-ethoxyethanol, diethylene glycol monoethylether and triethyleneglycol monomethylether. Especially preferred polyols comprise glycerol or sorbitol and related compounds which are capable also of acting as a humectant. The proportion of a mono, di or polyol in the formulation is often selected in the range of up to 15%, and in a number of instances from 0.5 to 12%, conveniently up to about 5% and preferably from about 0.2 to 3%.

In certain preferred embodiments of the present invention, the compositions are in the form of emulsions in which the continuous phase comprises from 10 to 35% volatile silicone oil, and from 5 to 15% non-volatile hydrophobic oil, the disperse phase comprises from 40 to 75%, the antiperspirant or deodorant active comprises from 1 to 35%, the wax structurant comprises from 7 to 25%, the emulsifier comprises from 0.1 to 10%, and the composition preferably contains up to 5% insoluble particulate materials, % s being by weight based on the composition.

By the employment of a composition of constituents selected within the ranges specified immediately hereinabove for such preferred embodiments, it is possible to produce an antiperspirant or deodorant emulsion stick exhibiting a combination of two or more beneficial properties, from the list of avoiding or ameliorating visible deposits, avoiding or ameliorating filmy deposits, avoiding or ameliorating drag, avoiding or ameliorating stickiness, and improving or retaining consumer-acceptable glide, whilst continuing to enjoy an acceptable stick hardness. In other words, it is possible to produce a stick from an emulsion which is structured using the invention wax and which exhibits a number of attributes which are well liked by consumers.

The relative proportions of the aqueous and oil phases in said preferred embodiments are carefully chosen so as to achieve a balance of properties. The proportion of the aqueous phase is normally within the range of from 30 to 70% by weight, taking into account any material present which is dissolved in or forms a single phase with water. Preferably, the aqueous phase constitutes not more than 65 wt % of the composition and in many desirable embodiments is in the range of from 45 to 60 wt %. Many favoured compositions contain in the region of 50 wt % aqueous phase.

The content of water in the aqueous phase of said preferred embodiments is often from 40 to 75 wt % of the phase, and often not more than 65 wt %. In practice, the proportion of water is often from 20 to 40 wt % of the composition and in many instances from 24 to 36 wt %.

The presence of a significant proportion of water in an emulsion is commonly expected to be perceived by the consumer as having wet and cooling attributes. However, and surprisingly, the instant emulsion sticks of the preferred embodiments have been perceived to resemble anhydrous sticks in those attributes.

The aqueous phase in an emulsion commonly contains, in addition to water, the antiperspirant or water-soluble deodorant. The proportion of such materials is usually at least 0.5 wt %, often at least 2 wt %, and in many instances at least 5 wt % and in the same or other instances is up to 30 wt %. The antiperspirant is preferably present in said preferred embodiments in an amount of at least 10 wt % and in many preferred emulsions between 20 and 25 wt %.

It can be desirable to incorporate in said preferred emulsion embodiments a minor proportion of a C2 to C6 dihydric or polyhydric aliphatic alcohol, for example in a proportion of up to half the weight of water in the aqueous phase. Normally, the proportion of such a di or polyhydric alcohol is from 0 to 15 wt %, and especially from 3 to 12 wt % of the emulsion. Examples of preferred dihydric or polyhydric alcohols include propylene glycol, glycerol or sorbitol. By restricting to incorporation of only a minor proportion of such alcohols, it is possible to further constrain the extent of cooling arising from the aqueous phase and the extent of evaporation and concomitant appearance of visible deposits, without the composition suffering from undue stickiness or other negative sensory attributes that can arise from employing such compounds in an emulsion as the major fluid constituent of the lyophobic phase. Some particularly preferred emulsions contain from 3 to 10 wt % glycerol.

Although one of the benefits of the emulsions of the instant invention is that the emulsions do not exhibit great cooling, the extent of cooling can be controlled by incorporating a chosen proportion of a volatile monohydric aliphatic alcohol such as ethanol or isopropanol, for example selected in the range of up to 5 wt %, eg at least 0.1 wt %. Many particularly preferred formulations within the class of preferred embodiments, however, are free from volatile alcohols.

The hydrophobic carrier liquids employed in said preferred embodiments of the invention emulsions comprise a mixture of a volatile silicone oil and a non-volatile oil, the proportions of the two constituents being selected within prescribed ranges.

In said preferred embodiments, the proportion of volatile silicone oil is preferably not higher than 25 wt % and often within the range of from 10 to 20 wt %. The proportion of non-volatile oil is preferably at least 8 wt % and in many instances is not more than 12 wt %. It is desirable to consider not only the absolute proportion of the oils in the emulsion, but also their relative proportions. Preferably, the volatile silicone oil is present in a weight ratio to the non-volatile oil of at least 1:1 and especially at least 5:4. The ratio is preferably not higher than 3:1 and more preferably not higher than 2:1. By carefully considering the ratio as well as the absolute proportions of the volatile silicone and non-volatile oils, it is possible to combine the benefits of reducing visible deposits, and simultaneously avoiding excess drag and greasiness for the emulsion.

It is further desirable to consider their ratio to the materials which contribute to visible deposits, such as any astringent salt (eg the antiperspirant salt) and/or the wax structurant. It is preferable for the weight ratio of antiperspirant salt to non-volatile oil in the preferred embodiments to be selected within the range of from 1:1 to 4:1 and especially from 2:1 to 10:3, whilst retaining the absolute proportion of the non-volatile oil within the proportions described hereinabove.

In selecting the non-volatile oils for use in said preferred embodiments, it is desirable to consider the various non-volatile oils described hereinbefore, including particularly the non-volatile silicone oils, liquid aliphatic hydrocarbons and aromatic esters. Other non-volatile oils which can be considered to provide a fraction of the non-volatile constituent for example up to 30% wt of that constituent for lower melting point waxes, such as those at up to 65 C, but possibly at least a major fraction for higher melting point waxes such as those at 70 C or higher, may comprise aliphatic ester oils containing at least one long chain alkyl group, such as esters derivable from $C_1$–$C_{20}$ alkanols esterified with a $C_8$ to $C_{22}$ alkanoic acid or $C_6$ to $C_{10}$ alkanedioic acid. The alkanol and acid moieties or mixtures thereof are preferably selected such that they have a melting point of below 20° C. Suitable esters include isopropyl myristate, lauryl myristate, isopropyl palmitate, diisopropyl sebacate and diisopropyl adipate. Other classes of such non-volatile oils like the aliphatic esters include aliphatic branched fatty alcohol oils containing at least 12 and preferably up to 30 carbons, such as isostearyl alcohol or octyldodecanol and liquid aliphatic ethers derivable from at least one fatty alcohol, such as myristyl ether derivatives e.g. PPG-3 myristyl ether or lower alkyl ethers of polyglycols such as PPG-14 butyl ether.

It is desirable to include in invention compositions and especially in emulsions at least one particulate insoluble material of small particle size, preferably in a proportion of up to 5 wt %, and particularly from 1 to 5 wt %. Such insoluble materials can be inorganic, such as talc, finely divided silica or clay. Alternatively, the material can be small particulate solid hydrocarbons such as finely divided polyethylene. The presence of such a constituent can improve the glide of the stick. In suspension formulations, this material can be in addiiton to any particulate antiperspirant salt.

Optional ingredients in the invention compositions can include disinfectants, for example at a concentration of up to about 10% w/w. Suitable deodorant actives can comprise deodorant effective concentrations of antiperspirant metal salts, deoperfumes, and/or microbicides, including particularly bactericides, such as chlorinated aromatics, including biguanide derivatives, of which materials known as Igasan DP300™, Triclosan™, Triclorban™ and Chlorhexidine warrant specific mention. A yet another class comprises biguanide salts such as available under the trademark Cosmosil™.

Other optional ingredients include wash-off agents, often present in an amount of up to 10% w/w to assist in the removal of the formulation from skin or clothing. Such wash-off agents are typically non-ionic surfactants such as esters or ethers containing a C8 to C22 alkyl moiety and a hydrophilic moiety which can comprise a polyoxyalkylene group (POE or POP) and/or a polyol.

A further optional constituent of the formulations comprises one or more secondary structurants which can be employed in addition to the ester (the primary structurant). The amount of such secondary structurants in the formulation is often 0, and usually not more than 15% of the formulation. It is commonly not greater than the amount of the primary structurant. It will be recognised that in many of the preferred embodiments in the form of emulsions, such a secondary structurant is either not present or is not needed.

The secondary structurants employable herein can be non-polymeric or polymeric. Non-polymeric structurants, sometimes referred to as gellants, can be selected from fatty acids or salts thereof, such as stearic acid or sodium stearate or 12-hydroxystearic acid. Other suitable gellants can comprise dibenzylidene alditols, e.g. dibenzylidene sorbitol. Further suitable gellants can comprise lanosterol, selected n-acyl amino acid derivatives, including ester and amide derivatives, such as N-lauroyl glutamate dibutylamide, which gellants can be contemplated in conjunction with hydroxystearic acid or an ester or amide derivative thereof. Still further gellants include amide derivatives of di or tribasic carboxylic acids, such as alkyl N,N' dialkylsuccinamides, e.g. dodecyl N,N'-dibutylsuccinamide. Stearyl alcohol and/or a natural plant or animal derived wax or similar synthetic waxes can be employed, if desired, as secondary structurant.

In some embodiments, the secondary structurant comprises candellila wax or esterified candellila wax, obtainable by esterifying pendant carboxylic acid group or groups in the wax with an fatty alcohol, preferably containing from 12 to 36 carbons, and especially containing from 16 to 24 carbon atoms. The weight ratio of primary wax to secondary candellila or esterified candellila wax is conveniently up to 1:4, and in a number of instances at least 10:1, such as 3:1, 1:1 and 1:3. Such combinations tend to demonstrate stick hardness that is greater than for corresponding formulations employing candellila wax alone as the structurant.

Polymeric structurants which can be employed can comprise organo polysiloxane elastomers such as reaction products of a vinyl terminated polysiloxane and a cross linking agent or alkyl or alkyl polyoxyalkylene-terminated poly (methyl substituted) or poly(phenyl substituted) siloxanes. A number of polyamides have also been disclosed as structurants for hydrophobic liquids. If the composition comprises an aqueous phase, this phase can be structured by polyacrylamides, polyacrylates or polyalkylene oxides.

Preferably, the formulations herein, including the preferred emulsion embodiments, are substantially free from solid fatty alcohols, typically water-insoluble, and often containing from 12 to 30 carbons, such as stearyl alcohol or behenyl alcohol, for example below 2 wt % and especially below 0.5 wt %.

The compositions herein can also incorporate one or more cosmetic adjuncts conventionally contemplatable for antiperspirant solids or soft solids. Such cosmetic adjuncts can include skin feel improvers, such as talc or finely divided polyethylene, for example in an amount of up to about 10% w/w; skin benefit agents such as allantoin or lipids, for example in an amount of up to 5% w/w; colours; skin cooling agents other than the already mentioned alcohols, such as menthol and menthol derivatives, often in an amount of up to 2% w/w. A commonly employed adjunct comprises a perfume, which is normally present at a concentration of from 0 to 4% and in many formulations from 0.25 to 2%.

The compositions described herein can be produced by conventional processes for making suspension or emulsion solids or soft-solids.

Thus, according to a further aspect of the present invention there is provided process for the production of an antiperspirant stick comprising the steps of:

1. incorporating into a liquid carrier an organic wax having a melting point of from 40 to 90° C. of which at least 60% of the weight of the wax is provided by at least one aliphatic ester satisfying the formula:

$$CH_3-(CH_2)_n-CO-(CH_2)_m-CH_3$$

in which n is from 9 to 39 and m is from 0 to 35,
in an amount sufficient to thicken or structure the carrier to produce an extrudable solid or a solid, 2. rendering the structurant-containing mixture mobile at an elevated temperature 3. mixing the liquid carrier with an antiperspirant active, steps 2 and 3 being conducted either before after or simultaneously with step 1 to form a structurant-containing mixture 4. introducing the mobile mixture into a dispensing container and 5. cooling or permitting the mobile mixture to cool to a temperature at which it is thickened or structured.

A convenient process sequence for suspension antiperspirant formulations comprises first mixing the wax with the carrier at a temperature that is high enough to melt the wax. Thereafter, particulate antiperspirant active can be blended with the carrier solution and the blend introduced, at a temperature that is often 5 to 10° C. above its setting temperature into its dispensing container, such as a barrel using suitable filling processes and is cooled or allowed to cool to ambient.

A suitable process for making emulsion antiperspirant formulations comprises forming a mobile mixture of the wax and the hydrophobic carrier, for example as in preparation of a suspension stick. Separately, an aqueous or hydrophilic phase is prepared, by introduction of antiperspirant active into the phase (if necessary, since such actives can conveniently be supplied in aqueous solution). The solution is preferably heated to a temperature similar to that of the oil phase and the phases are thereafter mixed. Alternatively, the hydrophylic phase can be introduced into the oil phase with gentle heating of the mixture and at a rate which maintains the elevated temperature of the mixture. The mixture is thereafter filled/cooled in a similar manner to that for suspension sticks.

The preferred emulsion embodiments can be made by the following process;

forming a hydrophobic mixture by mixing a volatile silicone oil, a non-volatile oil and a wax structurant at an elevated temperature or bringing the mixture to the elevated temperature at which the structurant melts or is dissolved or dispersed in the oils, thereby forming a mobile hydrophobic mixture, simultaneously or sequentially forming an aqueous phase containing water soluble or miscible constituents, shear mixing the mobile hydrophobic mixture with the aqueous phase in the presence of an emulsifier, and any insolble particulate materials thereby forming an emulsion comprising a hydrophobic continuous phase and a disperse aqueous phase, cooling or permitting the emulsion to cool to a temperature at which a solid is formed by the structurant structuring the continuous phase, characterised in that the continuous phase comprises from 10 to 35% volatile silicone oil, and from 5 to 15% non-volatile hydrophobic oil, the disperse phase comprises from 40 to 75%, the antiperspirant or deodorant active comprises from 0.5 to 35%, the wax structurant comprises from 7 to 25%, the emulsifier comprises from 0.1 to 10%, the composition preferably contains up to 5% insoluble particulate materials, % s being by weight based on the composition.

The emulsion formulations described herein can be made by any of the processes hitherto described or used for making antiperspirant emulsions containing a high internal phase volume, such as at least 40 wt % internal phase.

One suitable process comprises 1. incorporating into the wax into a mixture of the volatile silicone and non-volatile oil in an amount sufficient to thicken or structure the oil phase,
2. rendering the structurant-containing mixture mobile at an elevated temperature, steps 1 and 2 being conducted in sequence or simultaneously
3. obtaining an aqueous solution of the antiperspirant or deodorant, optionally containing an emulsifier,
4. mixing the mobile material produced in step 2 with the aqueous solution of step 3 in the presence of an emulsifier and with shear to form an emulsion at an elevated temperature
5. introducing the emulsion whilst still mobile mixture into a dispensing container and
6. cooling or permitting the emulsion to cool to a temperature at which it solidifies.

In step 2, it is highly desirable to maintain the mixture at the chosen elevated temperature until the wax has been completely dispersed thoughout the oil phase and at a temperature which is often 5 to 10° C. above the melting point of the highest melting wax.

In step 3, it is often convenient to introduce an emulsifier into a pre-formed solution containing the antiperspirant salt, but in other instances, a solid antiperspirant can be dissolved in the aqueous phase. The step is often carried out at elevated temperature or the solution is heated to elevated temperature before being mixed in step 4 with the mobile oil phase. The aqueous phase is often heated to within 20° C. of the oil phase.

In step 4, the two liquid phases are mixed together under shear conditions and in the presence of an emulsifier. By so doing, droplets of the dispersed phase are obtained. This step is carried out at a temperature maintained above the solidification temperature of the formulation, and is often selected in the range of from about 50 to 70° C., depending on its constituents.

In step 5, the mobile emulsion in step 4 is introduced into stick dispensers, often called barrels. This can be carried out using conventional cast methods, or alternatively an injection moulding technique may be employed as described in PCT application no PCT/EP 99/07249. Likewise, the mobile suspension produced iun step 3 of the suspension route can be injected under pressure into barrels, preferably at a temperature within the range of 3° C. about the regular setting temperature of the formulation.

In step 6, the dispensers containing the mobile emulsion are either subjected to forced cooling, for example by being passed though a cooling tunnel or may be simply allowed to cool in ambient air, for example if they have been filled in step 5 (or step 4 in the suspension route) by an injection moulding technique that is operated within 3° C. of the normal setting temperature of the formulation.

The compositions herein are suitable for applying topically to human skin, and particularly antiperspirant compositions to axillae, thereby reducing observable perspiration.

Thus, according to a third aspect of the present invention, there is provided a method for preventing or reducing perspiration on human skin comprising topically applying to the skin an antiperspirant composition comprising an antiperspirant active, a liquid carrier and a structurant which comprises an organic wax having a melting point of from 40 to 90° C. of which at least 60% of the weight of the wax is provided by at least one aliphatic ester satisfying the formula:

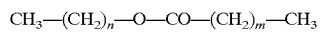

$$CH_3-(CH_2)_n-O-CO-(CH_2)_m-CH_3$$

in which n is from 9 to 39 and m is from 0 to 35.

It is particularly desirable to apply topically the particularly preferred antiperspirant or deodorant emulsion composiitons, namely those comprising a continuous phase which comprises from 10 to 35% volatile silicone oil, and from 5 to 15% non-volatile hydrophobic oil, from 40 to 75% of ta disperse aqueous phase which contains from 1 to 35% of an antiperspirant or deodorant active, from 7 to 25% of a wax structurant, from 0.1 to 10% of an emulsifier, and preferably contains up to 5% insoluble particulate materials, %s being by weight based on the composition. Having described the invention in general terms, specific embodiments thereof will be described more fully by way of example only.

In preliminary trials, mixtures of each of the following hydrophobic oils were formed with 10% by weight of each the specified waxes and heated to elevated temperature at which all the wax had melted, and then permitted to cool to ambient temperature.

Oils—volatile silicones, Phenyl trimethicone, polyphenyl methoxysiloxane, isostearyl alcohol, octyl methoxycinnamate, PPG-14 Butylether, $C_{12-15}$ alkylbenzoate, mineral oil.

Waxes—K62, K66, K69, K82H and K82N

The resultant materials were all opaque gels which ranged from the softest, which was soft/hard through to the hardest, which was very hard.

EXAMPLES 1 TO 15 AND COMPARISONS C16 TO C18

In Examples 1 to 15 and Comparisons C16 to C18, suspension sticks according to the formulations summarised in Table 1 below were made by the following general method:

The oils were first combined to produce a carrier mixture. The wax was introduced into the carriers and dissolved by heating and stirring to a temperature of 80° C. to 100° C. and above the melting point of the wax. The resultant mobile mixture was then allowed to cool under gentle stirring, and the specified particulate antiperspirant active was then stirred in and fully dispersed. When the mixture had reached a temperature of about 5–10 degrees above its gelling point, it was then poured into stick barrels which were allowed to cool in a laboratory (in an ambient temperature environment) and solidify.

The constituents of the Examples were as follows:
(1) vol.sil—DC345 (Dow Corning Inc)
(2) vol.sil—DC245 (Dow Corning Inc)
(3) octylisononanoate—(Stepan)
(4) PPG-14 Butylether—Fluid AP (Amercol).
(5) $C_{12-15}$ Alkyl Benzoate—Finsolv TN (Fintex).
(6) Polydecene—Silkflo 364NF (Albermarle)
(7) Dimethicone—DC 350 (Dow Corning Inc)
(8) PEG-8 distearate—Estol E04DS 3724 (Unichema)
(9) ECDC—Cetyl Dimethicone copolyol—Abil EM90 (Goldschmidt)
(10) Talc—Suprafino talc (Luzenac America Inc)
(11) AZAG—Al/Zr Tetrachlorohydrex glycine complex (Summit)
(12) AZCH—50% aqueous solution of Al/Zr pentachlorohydrate (Giulini)
(13) AZG 370—Al/Zr chlorohydrate glycine complex (Summit)
(14) K62—$C_{16-22}$ alkyl stearate behenate wax (MP 62° C.) (Koster Keunen)
(15) K69—$C_{18-38}$ alkyl acetate wax (MP 69° C.) (Koster Keunen)
(16) K82N—$C_{16-22}$ alkyl stearate behenate wax (MP 82° C.) (Koster Keunen)
(17) K82H—$C_{18-38}$ alkyl stearate wax(Koster Keunen)
(18) K62/K82H—2:1 weight ratio of K62 and K82H
(19) K80P—$C_{16-22}$ alkyl stearate behenate wax (MP 80° C.) (Koster Keunen) (Comparison wax)
(20) BW67—Stearyl beeswax (MP 67° C.) (Koster Keunen) (Comparison wax)
(21) SiBee—Siliconyl beeswax (Koster Keunen) (Comparison wax)
(22) Glycerol—(Aldrich)
(23) Hydrogenated polyisobutene—Panalene L 14E (Amoco)
(24) Cetearyl esterified candellilate wax (Koster Keunen)
(25) Decyl oleate—Cetiol V
(26) demineralised water
(27) Aluminium Zirconium pentachlorohydrate—Rezal 67
(28) Aluminium zirconium tetrachlorohydrex GLY—Zirconal 50
(29) finely divided particulate polyethylene—Acumist B18
(30) fragrance
(31) polyglycerol diisostearate—Lameform TGI
(32) polyglycerol polyricinoleate—Quest PGPR
(33) hydrogenated polyisobutene—Fancol 800
(34) hydrogenated polyisobutene—Fancol 250
(35) 32 carbon diguerbet—Lambent DG 3200
(36) Isohexadecane—Permethyl 101A In Table 1, SOFT indicates that the product was a soft solid with a penetrometer penetration of >50 mm whose deposit score could not be tested using the available apparatus. Hereinafter, sphere hardness indicates that the hardness was measured using a sphere indentation technique and penet hardness indicates that the hardness was measured by the depth of penetration of a needle, as described herein Comparison stick—Conventional wax structured (CWS) typically had a Sphere Hardness of 0.217 N/mm$^2$ and a Deposit score on Black Wool of 61 in the tests described herein.

TABLE 1

| Example No | 1 | 2 | 3 | 4 | 5 | 6 | 7 | 8 | 9 |
|---|---|---|---|---|---|---|---|---|---|
| Constituent | Weight % in formulation | | | | | | | | |
| vol sil ($^1$) | 54.55 | 48.49 | 54.55 | 60.00 | 54.55 | 54.55 | 51.0 | | |
| vol sil ($^2$) | | | | | | | | 66.75 | 49.75 |
| Octyl-iso-nonanoate ($^3$) | 6.75 | 6.00 | 6.75 | | | | | | |
| PPG-14 Butyl ether ($^4$) | | | | | | | | 15.0 | 15.0 |
| $C_{12-15}$ Alkyl Benzoate ($^5$) | | | | 6.00 | | | | | |
| Polydecene ($^6$) | | | | | | 6.75 | | | |
| Dimethicone ($^7$) | | | | | 6.75 | | | | |
| PEG-8 distearate ($^8$) | | | | | | | | | |
| ECDC ($^9$) | | | | | | | | 4.5 | 4.5 |
| Talc ($^{10}$) | 3.94 | 3.50 | 3.94 | | 3.94 | 3.94 | | | |
| AZAG ($^{11}$) | 24.76 | 22.0 | 24.76 | 24.0 | 24.76 | 24.76 | 24.0 | | |
| AZG 370 ($^{13}$) | | | | | | | | 20.0 | 20.0 |
| K62 ($^{14}$) | 10.0 | | | 10.0 | 10.0 | 10.0 | | 8.0 | 10.0 |
| K69 ($^{15}$) | | 10.0 | | | | | | | |
| K82N ($^{16}$) | | | | | | | 10.0 | | |

TABLE 1-continued

| | | | | | | | | | |
|---|---|---|---|---|---|---|---|---|---|
| K62/K82H (18) | | 20.0 | | | | | | | |
| K80P (19) | | | | | | | | | |
| BW67 (22) | | | | | | | | | |
| SiBee (21) | | | | | | | | | |
| Fragrance | | | | | | | | 0.75 | 0.75 |
| Sphere Hardness (N × 10⁻³/mm²) | 224 | 183 | 320 | 98 | 201 | 190 | 33 | | |
| Penetration Hardness mm | | | | | | | | 16.1 | 12.1 |
| Deposit Score Black Wool | 19 | 16 | 42 | nm | 29 | 53 | 25 | 39 | 54 |

| Example No | 10 | 11 | 12 | 13 | 14 | 15 | C16 | C17 | C18 |
|---|---|---|---|---|---|---|---|---|---|
| Constituent | | | Weight % in formulation | | | | | | |
| vol sil (1) | | | | | | | 54.55 | 54.55 | 54.55 |
| vol sil (2) | 61.75 | 49.75 | 51.75 | 57.75 | 54.75 | 59.75 | | | |
| Octyl-iso-nonanoate (3) | | | | | | 5.0 | 6.75 | 6.75 | 6.75 |
| PPG-14 Butyl ether (4) | 5.0 | | 15.0 | | 10.0 | | | | |
| C₁₂₋₁₅ Alkyl Benzoate (5) | | 15.0 | | 5.0 | | | | | |
| Polydecene (6) | | | | | | | | | |
| Dimethicone (7) | | | | | | | | | |
| PEG-8 distearate (8) | 4.5 | 4.5 | 4.5 | 4.5 | 4.5 | 4.5 | | | |
| ECDC (9) | | | | | | | | | |
| Talc (10) | | | | | | | 3.94 | 3.94 | 3.94 |
| AZAG (11) | | | | | | | 24.76 | 24.76 | 24.76 |
| AZG 370 (13) | 20.0 | 20.0 | 20.0 | 20.0 | 20.0 | 20.0 | | | |
| K62 (14) | | | | | | | | | |
| K69 (15) | 8.0 | 10.0 | | | 10.0 | | | | |
| K82N (16) | | | 8.0 | 10.0 | | 10.0 | | | |
| K62/K82H (18) | | | | | | | | | |
| K80P (19) | | | | | | | 10.00 | | |
| BW67 (22) | | | | | | | | 10.00 | |
| SiBee (21) | | | | | | | | | 10.00 |
| Fragrance | 0.75 | 0.75 | 0.75 | 0.75 | 0.75 | 0.75 | | | |
| Sphere Hardness (N × 10⁻³/mm²) | | | | | | | SOFT | SOFT | SOFT |
| Penetration Hardness mm | 19.8 | 18.8 | 30.4 | 13.8 | 16.5 | 13.8 | | | |
| Deposit Score Black Wool | 39 | 29 | 30 | 49 | 3 5 | 49 | SOFT | SOFT | SOFT |

From Table 1, all the products obtained in the Examples had a measurable hardness, in contrast with the products obtained with a similar proportion of the three comparison waxes, (C16 to C18) demonstrating the superior capability of the invention waxes compared with the comparison modified beeswaxes to structure an antiperspirant composition, and particularly volatile silicone-containing formulations.

It will be seen that the products of the present invention usually caused significantly lower white deposits in comparison with a conventional wax-structured (stearyl alcohol) suspension antiperspirant composition (CWS). On the other hand, the products of the comparison waxes in C16–C18 were too soft for white deposits to be measured by the method above.

In a further test, the formulation of Example 1 was compared in a head to head test with the CWS comparison stick by a trained panel of assessors. One product was applied to one axilla and the other product was applied to the other axilla. Left/right applications were balanced. The difference in visible white deposit score was 16 in favour of the invention formulation (48/64) confirming the results obtained by applying the products to a non-skin substrate. This difference is statistically significant at greater than the 95% confidence level.

EXAMPLES 19 to 31

In these Examples, emulsion sticks having formulations as summarised in Table 2 below were made by one or other of the following general methods:

A continuous oil phase was prepared by introducing the wax into a mixture of the oils and the emulsifier. The mixture was heated to the range of 80° C. to 100° C. and then maintained in the range of up to approximately 10° C. above the melting point of the wax, with gentle mixing (low shear) in a Silverson mixer until the wax had dissolved. The mixture was allowed to cool to about 80° C. in Examples 19 to 23. A disperse phase (also referred to as the internal phase) was prepared by heating a solution of aluminium zirconium active antiperspirant in water or a mixture of water and polyol to a similar temperature as the continuous oil phase.

In Examples 19 to 23, the hot disperse phase was introduced under high shear mixing conditions into the continuous phase. High shear mixing was continued until the mixture had reached a pour temperature of about 5 to 10 degrees above formulation set temperature, poured in the stick barrels and allowed to cool naturally to ambient laboratory temperature. In Examples 24 to 31, the hot disperse phase was introduced slowly into the oil phase whilst progressively increasing the mixing speed of the Silverson mixer. When the disperse phase had been completely introduced, the formulation was mixed at higher speed for a further 5 minutes, then mixed at a slower speed until it had reached about 10–15° C. above the formulation set temperature, at which point it was poured in the stick barrels and allowed to cool naturally to ambient laboratory temperature.

TABLE 2

| Example No | 19 | 20 | 21 | 22 | 23 | 24 | 25 | 26 |
|---|---|---|---|---|---|---|---|---|
| Constituent | | | | Weight % in formulation | | | | |
| vol sil ($^1$) | 38.92 | 34.50 | 30.08 | | | | | |
| vol sil ($^2$) | | | | 25.65 | 25.65 | 21.48 | 19.49 | 16.31 |
| Octyl-iso-nonanoate ($^3$) | 5.08 | 4.50 | 3.92 | 3.35 | 3.35 | | | |
| Polydecene ($^6$) | | | | | | 27.15 | 24.64 | 20.61 |
| PPG-14 butyl ether ($^4$) | | | | | | 5.37 | 4.87 | 4.08 |
| ECDC ($^9$) | 1.0 | 1.0 | 1.0 | 1.0 | 1.0 | 1.0 | 1.0 | 1.0 |
| AZCH ($^{12}$) | 50.0 | 50.0 | 50.0 | 50.0 | 50.0 | 30.0 | 30.0 | 30.0 |
| Glycerol ($^{22}$) | | | | | | | | |
| Water | | | | | | | | |
| K62 ($^{14}$) | 5.0 | | | 20.0 | | 15.0 | 20.0 | 28.0 |
| K69 ($^{15}$) | | | | | 20.0 | | | |
| K82N ($^{16}$) | | 10.0 | | | | | | |
| K62/K82H ($^{18}$) | | | 15.0 | | | | | |
| Internal phase | 50 | 50 | 50 | 50 | 50 | 30. | 30 | 30 |
| Sphere Hardness (N × 10$^{-3}$/mm$^2$) | 6 | 44 | 37 | | | 0.05 | 0.12 | 0.25 |
| Penetrometer Hardness mm | | | | 8.4 | 8.2 | 14.4 | 8.2 | 3.7 |
| Deposit Score Black Wool | 14 | 20 | 21 | 28 | 28 | 25 | 23 | 18 |

| Example No | 27 | 28 | 29 | 30 | 31 | 32 | 33 | 34 | 35 |
|---|---|---|---|---|---|---|---|---|---|
| Constituent | | | | | Weight % in formulation | | | | |
| vol sil ($^1$) | | | | | | | | | |
| vol sil ($^2$) | 17.5 | 15.51 | 13.92 | 11.54 | 7.65 | 9.15 | 7.96 | 6.76 | 3.58 |
| Octyl-iso-nonanoate ($^3$) | | | | | | | | | |
| Polydecene ($^6$) | 22.12 | 19.61 | 17.60 | 14.58 | 9.55 | 11.56 | 10.05 | 8.55 | 4.52 |
| PPG-14 butyl ether ($^4$) | 4.38 | 3.88 | 3.48 | 2.88 | 1.89 | 2.29 | 1.99 | 1.69 | 0.90 |
| ECDC ($^9$) | 1.0 | 1.0 | 1.0 | 1.0 | 1.0 | 1.0 | 1.0 | 1.0 | 1.0 |
| AZCH ($^{12}$) | 40.0 | 40.0 | 40.0 | 40.0 | 40.0 | 40.0 | 40.0 | 40.0 | 40.0 |
| Glycerol ($^{22}$) | | | | 5.0 | 10.0 | 10.0 | 15.0 | 15.0 | 5.0 |
| Water | | | | 5.0 | 10.0 | 10.0 | 15.0 | 15.0 | 15.0 |
| K62 ($^{14}$) | 15 | 20 | 24 | 20.0 | 20.0 | 16.0 | 9.0 | 12.0 | 20.0 |
| K69 ($^{15}$) | | | | | | | | | |
| K82N ($^{16}$) | | | | | | | | | |
| K62/K82H ($^{18}$) | | | | | | | | | |
| Internal phase | 40 | 40 | 40 | 50 | 60 | 60 | 70 | 70 | 70 |
| Sphere Hardness (N × 10$^{-3}$/mm$^2$) | 0.05 | 0.16 | 0.18 | 0.21 | 0.21 | 0.10 | 0.04 | 0.09 | 0.20 |
| Penetrometer Hardness mm | 13.6 | 5.8 | 5.1 | 4.5 | 5.0 | 7.7 | 12.4 | 12.3 | 4.8 |
| Deposit Score Black Wool | 23 | 24 | 17 | 19 | 17 | 22 | 18 | 16 | 18 |

EXAMPLES 32 to 36

In these Examples, formulations as summarised in Table 3 below and containing a low proportion of structurant were prepared by the following general method:

The volatile silicone, oil and wax structurant were mixed in a Silverson mixer at 3000 rpm whilst being heated to approximately 70° C. Particulate materials were introduced under the same conditions, and then the stirrer speed was reduced to 1000 rpm whilst the mixture was allowed to cool to about 57° C. Thereafter, the mixture was allowed to cool to ambient temperature without further stirring.

TABLE 3

| Example No | 36 | 37 | 38 | 39 | 40 | 41 |
|---|---|---|---|---|---|---|
| Constituent | | | Weight % in formulation | | | |
| Vol sil ($^2$) | 61.5 | 65.75 | 61.5 | 65.75 | 61.5 | 65.75 |
| Octyl-iso-nonanoate ($^3$) | 7.25 | | | | | |
| C$_{12-15}$ Alkyl Benzoate ($^5$) | | 7.25 | | | | |
| PPG-14 Butyl ether ($^4$) | | | 7.25 | | | |
| Polydecene ($^6$) | | | | 7.25 | | |
| Dimethicone ($^7$) | | | | | 7.25 | |
| Polyisobutene ($^{23}$) | | | | | | 7.25 |
| Talc ($^{10}$) | 4.25 | 4.25 | 4.25 | | | |

TABLE 3-continued

| AZAG ($^{11}$) | 24.0 | 24.0 | 24.0 | 24.0 | 24.0 | 24.0 |
|---|---|---|---|---|---|---|
| K62 ($^{14}$) | 3.0 | 3.0 | 3.0 | 3.0 | 3.0 | 3.0 |

The formulations produced in these Examples were all in the form of soft solids.

EXAMPLES 42 to 44

In these Examples, Example 1 was repeated, but employing instead of solely its beeswax ester, a combination of the beeswax ester and an esterified candellilate wax in the proportions summarised in Table 4 below, together with the properties of the resultant formulations.

TABLE 4

| Example No | 42 | 43 | 44 |
|---|---|---|---|
| Constituent | % w/w in formulation | | |
| K62($^{14}$) | 2.5 | 5.0 | 7.5 |
| Esterified Candellilate Wax($^{24}$) | 7.5 | 5.0 | 2.5 |
| Non-wax constituents according to Ex 10 | 90 | 90 | 90 |

TABLE 4-continued

| Example No | 42 | 43 | 44 |
|---|---|---|---|
| Properties | | | |
| Penetrometer Hardness mm | 11.7 | 19.7 | 7.5 |
| Deposit Score Black Wool | 53 | 56 | 60 |

The properties of number of the sticks summarised in the foregoing Tables were analysed obtained by the methods described hereinbelow and the results summarised in the Table. The evaluations were made after the sticks had been stored for at least 24 hours at laboratory room temperature.

The resultant materials were all opaque gels which ranged from soft/hard, which was the softest, through to very hard, which was the hardest.

EXAMPLES 46 TO 51 AND COMPARISONS C45 AND C52

Example formulations 46 to 51 and Comparison C45 were made by the following general method:

A continuous oil phase was prepared by introducing the wax into a mixture of the oils and the emulsifier. The mixture was heated to the range of 80° C. to 100° C. and then maintained in the range of up to approximately 10° C. above the melting point of the wax, with gentle mixing (low shear) in a Silverson mixer until the wax had dissolved. The mixture was allowed to cool to about 80° C. A disperse phase (also referred to as the internal phase) was prepared by heating a solution of aluminium zirconium active antiperspirant in water or a mixture of water and polyol to a similar temperature as the continuous oil phase.

The hot disperse phase was introduced slowly into the oil phase whilst progressively increasing the mixing speed of the Silverson mixer. When the disperse phase had been completely introduced, the formulation was mixed at higher speed for a further 5 minutes, then mixed at a slower speed until it had reached about 10–15° C. above the formulation set temperature, at which point it was poured in the stick barrels and allowed to cool naturally to ambient laboratory temperature.

The formulations and their attributes are summarised in the following Table 5, except for comparison C52 which is conventional wax structured suspension antiperspirant stick. The term u/a indicates underarm.

TABLE 5

| Ingredient | C45 | 46 | 47 | 48 | 49 | 50 | 51 | C52 |
|---|---|---|---|---|---|---|---|---|
| vol sil 1 | 30.65 | 12.6 | 12.6 | 12.6 | 18.5 | 12.6 | 12.6 | |
| oil 4 | 3.35 | — | — | — | — | — | — | |
| oil 5 | — | 8.4 | 8.4 | 8.4 | 12.5 | — | — | |
| oil 25 | — | — | — | — | — | 8.4 | — | |
| oil 23 | — | — | — | — | — | — | 8.4 | |
| emulsifier 9 | 1.0 | 1.0 | 1.0 | 1.0 | 1.0 | 1.0 | 1.0 | |
| Water 26 | — | — | 4.5 | 4.5 | 4.5 | 4.5 | 4.5 | |
| Glycerol 22 | — | 4.5 | — | — | — | — | — | |
| Talc 10 | — | — | — | 2.0 | 2.0 | 2.0 | 2.0 | |
| AZCH 27 | — | 58.0 | 58.0 | 58.0 | — | 58.0 | 58.0 | |
| AZCH 28 | 50.0 | — | — | — | 48.0 | — | — | |
| wax 14 | 15.0 | 12.5 | 12.5 | 12.5 | 12.5 | 12.5 | 12.5 | |
| PE 29 | — | 2.0 | 2.0 | — | — | — | — | |
| oil 30 | — | 1.0 | 1.0 | 1.0 | 1.0 | 1.0 | 1.0 | |

TABLE 5-continued

| Ingredient | C45 | 46 | 47 | 48 | 49 | 50 | 51 | C52 |
|---|---|---|---|---|---|---|---|---|
| Characterisation | | | | | | | | |
| Hardness (mm) | 8.4 | 5.9 | 5.7 | 5.7 | 7.4 | 4.1 | 6.1 | 7.3 |
| Whiteness Wool (0h) | 13 | 18 | 18 | 20 | | | | 36 |
| Wool (24h) | 72 | 27 | 32 | 23 | | | | 87 |
| Key Sensory data | | | | | | | | |
| Cool | 10 | 30 | 32 | 41 | | | | 14 |
| Flakes | 17 | 1 | 9 | 10 | | | | 14 |
| Drag | 41 | 16 | 14 | 6 | | | | 11 |
| Cool (2 min) | 15 | 25 | 23 | 33 | | | | 12 |
| Glide (2 min) | 37 | 57 | 42 | 45 | | | | 49 |
| White visible deposits u/a | 25 | 7 | 12 | 11 | | 8 | | 51 |
| Filmy visible deposits u/a | 33 | 6 | 9 | 7 | | | | 38 |
| White deposits (30 min) u/a | 25 | 8 | 6 | 6 | | 5 | | 40 |
| Filmy deposits (30 min) u/a | 23 | 4 | 3 | 3 | | | | 18 |
| Glide (30 min) | 33 | 57 | 43 | 43 | | | | 43 |

EXAMPLES 53 TO 55

In Examples 53 to 55, further formulations were made using the method used for Example 46. The formulations are summarised in Table 6 below.

TABLE 6

| Ingredient | 53 | 54 | 55 |
|---|---|---|---|
| wax 14 | 15.0 | 15.0 | 15.0 |
| vol sil 1 | 16.8 | 14.7 | 12.6 |
| oil 5 | 4.2 | 6.3 | 8.4 |
| Glycerol 22 | 10.0 | 10.0 | 10.0 |
| Emulsifier 9 | 1.0 | 1.0 | 1.0 |
| PE 29 | 2.0 | 2.0 | 2.0 |
| AZCH 28 | 50.0 | 50.0 | 50.0 |
| oil 30 | 1.0 | 1.0 | 1.0 |
| Characterisation | | | |
| Hardness (mm) | 5.4 | 8.7 | 6.5 |
| Whiteness | | | |
| Wool (0 h) | 18 | 19 | 17 |
| Wool (24 h) | 16 | 17 | 17 |

EXAMPLES 56 TO 60

In Example 56 to 60 further formulations were made using the method used for Example 46. The formulations are summarised in Table 7 below.

TABLE 7

| Ingredient | 56 | 57 | 58 | 59 | 60 |
|---|---|---|---|---|---|
| vol sil 1 | 13.05 | 12.9 | 13.35 | 13.2 | 12.9 |
| oil 5 | 8.7 | 8.6 | 8.9 | 8.8 | 8.6 |
| wax 14 | 12.5 | 12.5 | 12.5 | 12.5 | 12.5 |

TABLE 7-continued

| Ingredient | 56 | 57 | 58 | 59 | 60 |
|---|---|---|---|---|---|
| PE 29 | 2.0 | 2.0 | 2.0 | 2.0 | 2.0 |
| Glycerol 22 | 4.5 | 4.5 | 4.5 | 4.5 | 4.5 |
| emulsifier 31 | 1.25 | 1.5 | — | — | — |
| emulsifier 32 | — | — | 0.75 | 1.0 | 1.5 |
| AZCH 27 | 58.0 | 58.0 | 58.0 | 58.0 | 58.0 |
| Hardness | | | | | |
| Penetration (mm) | 9.9 | 10.0 | 6.7 | 6.6 | 7.5 |

EXAMPLES 61 TO 65

In Example 561 to 65 further formulations were made using the method used for Example 46. The formulations are summarised in Table 8 below.

TABLE 8

| Ingredient | 61 | 62 | 63 | 64 | 65 |
|---|---|---|---|---|---|
| vol sil 1 | 12.6 | 12.6 | 12.6 | 12.6 | 12.6 |
| oil 36 | 8.4 | — | — | — | — |
| oil 33 | — | 8.4 | — | — | — |
| oli 34 | — | — | 8.4 | — | — |
| oil 35 | — | — | — | 8.4 | — |
| oil 6 | — | — | — | — | 8.4 |
| emulsifier 9 | 1.0 | 1.0 | 1.0 | 1.0 | 1.0 |
| AZCH 27 | 58.0 | 58.0 | 58.0 | 58.0 | 58.0 |
| Water 26 | 4.5 | 4.5 | 4.5 | 4.5 | 4.5 |
| wax 14 | 12.5 | 12.5 | 12.5 | 12.5 | 12.5 |
| Talc 10 | 2.0 | 2.0 | 2.0 | 2.0 | 2.0 |
| oil 30 | 1.0 | 1.0 | 1.0 | 1.0 | 1.0 |
| Hardness | | | | | |
| Penetration (mm) | 8.8 | 6.6 | 8.4 | 7.5 | 5.5 |
| Whiteness | | | | | |
| Wool (0 hr) | 29 | 21 | 23 | 17 | 19 |
| Wool (24 hr) | 68 | 26 | 26 | 21 | 16 |

Hardness Measurements by Sphere Indentation (Sphere Hardness)

The hardness of a solid or a soft solid can be measured using a sphere to indent its surface. The test apparatus can move a sphere into and away from a sample at a controlled speed and at the same time measure the applied force. The parameter which is determined as hardness is a function of the peak force and the projected area of indentation.

A specific test protocol used a desktop Instron Universal Testing Machine (Model 5566) fitted with a 10N load cell. A metal sphere of diameter 9.5 mm was fitted to the underside of the load cell such that it could be used for indenting a sample placed beneath it on the base plate of the instrument. After the sample was positioned, the sphere position was adjusted until it was just above the sample surface. The Testing Machine's control software was used to generate the subsequent motion profile used in the test method. This profile initially indented the sphere into the sample at an indentation speed of 0.05 mm/s until a designated force was reached, which was chosen such that the depth of penetration into the sample was less than the radius of the sphere. At this load, the direction of motion of the sphere was reversed to withdraw the sphere from the sample at the same speed of 0.05 mm/s. During the course of the test, the data acquired were time (s), distance (mm) and force (N) and the data acquisition rate was 25 Hz.

Suitable samples for measurement were contained in stick barrels (having a screw mechanism). The stick was wound up until it protruded above the top edge of the barrel and then a knife was used to skim the top of the barrel in such a way as to leave a flat uniform surface. The stick was then wound back into the barrel as far as possible to minimise any mechanical interference resulting from compliance of the screw mechanism is the pack. Two indents were generally made on either side of the screw. The data associated with each test were manipulated using standard spreadsheet software and used to calculate the hardness, H using the following equation:

$$H[N/mm^2]=F_{max}[N]/A_p[mm^2]$$

where $F_{max}$ is the peak load and $A_p$ is the projected area of the indentation remaining on unloading. This area can be calculated geometrically from the plastic indentation depth. This is slightly less than the total penetration depth measured under load because of elastic deformation of the sample. The plastic indentation depth is calculated from a graph of the unloading force versus total penetration depth. The initial slope of this unloading data depends on the initial elastic recovery of the sample. The plastic indentation depth is estimated from an intercept between the zero force axis and a straight line drawn at a tangent to the part of the unloading slope corresponding to plastic deformation.

Hardness Measurements by Penetrometer

Hardness measurements by a Lab Plant PNR 10 penetrometer were performed on a stick in the stick barrel using a Seta wax needle, mass=2.59, cone angle at the point of the needle specified to be 9°10'∓15' (ASTM D1321; IP376; DIN 51579), having a maximum drop of 50 mm. The stick was wound up to above the barrel surface, and then cut to leave a flat, uniform surface. The needle was carefully lowered to the stick surface, and then a penetration hardness measurement was conducted by allowing the needle in its holder to drop under its combined weight of 50 g for a period of 5 seconds after which the penetration depth is noted. This process was carried out at six different points on the stick surface.

The hardness reading quoted is the average value of the 6 measurements.

An appropriate hardness for antiperspirant material intended for use in an open-ended dispensing container is less than 30 mm, particularly in the range of 5 to 20 mm.

Measurement of Deposits

The procedure involves instrumentally applying a sample of an AP stick to a substrate using a pay-off rig under standardised conditions and then measuring the mean level of white deposits using image analysis.

I) Application of the Sample to the Substrate

The substrate was a 12×28 cm strip of Worsted wool fabric.

The AP sticks were previously unused and with domed top surface unaltered.

The pay-off rig comprised a flat base on which a flat substrate was attached by a clip at each end. A pillar having a mounting to receive a standard size stick barrel was mounted on an arm that was moveable horizontally across the substrate under the control of a pnuematic piston. The mounting for the stick barrel was spring biased to provide the same vertical force of the stick on the substrate each time.

Each stick was temperature conditioned in the laboratory overnight before the measurement was made. The stick was laterally passed across the substrate eight times. The substrate was carefully removed from the rig and the deposit score, i.e. assessment of white deposits, measured straightaway using image analysis.

II) Image Analysis

The sample substrate was illuminated by high angle fluorescent tubes to remove shadowing. The image was recorded through a Sony XC77 camera with a Cosmicar 16 mm focal length lens. The camera was positioned vertically above a reference slide and the instrument calibrated. The sample substrate was placed under the camera and, an image captured. This was and then analysed using a Kontron IBAS image analyser to obtain the mean grey level. This notionally divided the image into a large array of pixels and measured the whiteness of each pixel. The whiteness was measured on a scale of 0 to 255, with 255 being whitest and 0 being black. It was assumed that low numbers indicate a clear deposit permitting the underlying substrate colour (grey or black) to be seen.

Sensory Properties

Sensory properties were evaluated by a panel of evaluators. Evaluators undergo extensive training to ensure the consistency and sensitivity of their sensory assessments, involving assessing a range of standard systems that exemplify various levels for each key sensory attribute. The sensory properties reported herein include coolness on application or after 2 minutes, flakiness, drag, glide and filmy deposits.

Product Application

Products are applied by evaluators in a measured dose of 300 mg+/−30 mg for sticks of coded formulations.

Protocol

Evaluators remove underarm hair 24 hours prior to testing. All testing is carried out in a controlled testing area, employing at least 14 evaluators. Evaluators are instructed to wash both their underarms and forearms with unperfumed Lux™ soap in luke warm water and to dry thoroughly before applying test products.

Evaluators apply the first product to their left underarm and complete the relevant score sheet. The strength and intensity of each product's sensory attributes are recorded on a descriptively anchored and divided 10 cm line scale. When the left underarm score sheet is completed, a second piece is applied to the right underarm and the process is repeated on a second score sheet. The evaluators' marks on the line scales are converted into scores on a 1–100 scale. Mean scores are then calculated for each sensory attribute for each product. Evaluators leave the products on their underarms unless any discomfort is reported.

What is claimed is:

1. An antiperspirant composition compris ing an antiperspirant active, a liquid carrier and a structurant or thickener for the carrier wherein the antiperspirant active is particulate, the carrier is anhydrous, thereby rendering the composition anhydrous, and the structurant or thickener comprises an organic wax having a melting point of from 40 to 90° C. of which at least 60% of the weight of the wax is provided by at lest one aliphatic ester satisfying the formula:

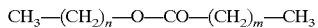

in which n is from 9 to 39 and m is from 0 to 35.

2. An antiperspirant composition according to claim 1 wherein at least 90% of the weight of the wax is provided by the said aliphatic ester.

3. An antiperspirant composition according to claim 1 wherein the wax contains less than 2% by weight free carboxylic acid.

4. An antiperspirant composition according to claim 1 wherein the wax contains less than 2% by weight hydrocarbons.

5. An antiperspirant composition according to claim 1 wherein in accordance with the general formula for the aliphatic ester, n is selected in the range of from 14 to 20 and m is selected within the range of 14 to 20.

6. An antiperspirant composition according to claim 5 wherein in accordance with the general formula for the aliphatic ester, m is selected within the range of 16 to 20.

7. An antiperspirant composition according to claim 1 wherein in accordance with the general formula for the aliphatic ester, n is selected in the range of from 18 to 38 and m is selected within the range of 0 or 1.

8. A composition according to claim 1 wherein the antiperspirant active comprises an aluminium, zirconium or aluminium/zirconium halohydrate, an activated aluminium, zirconium or aluminium/zirconium halohydrate, or an aluminium, zirconium or aluminium/zirconium complex or an activated aluminium, zirconium or aluminium/zirconium complex.

9. A composition according to claim 8 wherein the antiperspirant active is a mixed zirconium-aluminium chlorohydrate, an activated aluminium chlorohydrate or a complex of aluminium plus zirconium chlorohydrate and glycine, optionally activated.

10. A composition according to claim 1 wherein the proportion of antiperspirant active is from 5 to 40% by weight.

11. A composition according to claim 1 wherein contains a volatile silicone and optionally a non-volatile silicone and/or a liquid non-silicone hydrophobic organic carrier selected from hydrocarbons, hydrophobic aliphatic esters, aromatic esters, hydrophobic alcohols and hydrophobic ethers.

12. An antiperspirant composition comprising an antiperspirant active, a liquid carrier and a structurant or thickener for the carrier in the form of an emulsion wherein the structurant or thickener comprises an organic wax having a melting point of from 40 to 90° C. of which at least 60% of the weight of the wax is provided by at least one aliphatic ester satisfying the formula:

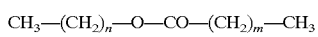

in which n is from 9 to 39 and m is from 0 to 35, wherein a continuous phase comprises from 10 to 35% volatile silicone oil, and from 5 to 15% non-volatile hydrophobic oil, a disperse phase comprises from 40 to 75%, the antiperspirant or deodorant active comprises from 0.5 to 35%, the wax structurant comprises from 7 to 25%, the emulsifier comprises from 0.1 to 10%, and the composition optionally contains up to 5% insoluble particulate materials % s being by weight.

13. A composition according to claim 12 wherein the disperse phase comprises from 40 to 65%.

14. A composition according to claim 12 comprising from 8 to 20% weight wax structurant.

15. A composition according to claim 12 comprising not more than 2% of a C12 to C24 saturated linear aliphatic alcohol.

16. A composition according to claim 12 comprising from 10 to 20% volatile silicone.

17. A composition according to claims wherein the non-volatile oil is selected from aliphatic esters, aromatic esters and hydrocarbons which are liquid at 25° C.

18. A composition according to claim 12 comprising the volatile silicone oil and non-volatile oil in a weight ratio of from 1:1 to 3:1.

19. A composition according to claim 12 comprising from 10 to 30% of a water-soluble antiperspirant active.

20. A composition according to claim 12 comprising the volatile silicone oil and non-volatile oil in a weight ratio of from 5:4 to 2:1.

21. A composition according to claim 12 comprising from 20 to 25% of a water-soluble antiperspirant active.

22. A composition according to claim 21 wherein the weight ratio of antiperspirant active to non-volatile oil is from 1:1 to 4:1.

23. A composition according to claim 12 comprising from 1 to 5% by weight of a particulate insoluble material.

24. A composition according to claim 23 containing a particulate insoluble material selected from talc, finely divided silica, clay, and particulate polyethylene.

25. A composition according to claim 12 comprising from 0.5 to 2% emulsifier.

26. A composition according to claim 12 further comprising up to 15% by weight of a polyhydric alcohol.

27. A composition according to claim 22 wherein the polyhydric alcohol is selected from glycerol, and propylene glycol.

28. A process for the production of an anhydrous antiperspirant stick comprising the steps of:
   1. incorporating into an anhydrous liquid carrier a structurant comprising an effective concentration of an organic wax having a melting point of from 40 to 90° C. of which at least 60% of the weight of the wax is provided by at least one aliphatic ester satisfying the formula:

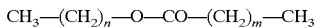

in which n is from 9 to 39 and m is from 0 to 35, in an amount sufficient to thicken or structure the carrier to produce an extrudable solid or a solid,
   2. rendering the structurant-containing mixture mobile at an elevated temperature
   3. mixing the liquid carrier with an antiperspirant active step 2 or 3 being conducted either before after or simultaneously with step 1 to form a structurant-containing mixture
   4. introducing the mobile mixture into a applicator container and
   5. cooling or permitting the mixture to cool to a temperature at which it is thickened or structured.

29. A process for forming an antiperspirant emulsion stick comprising
   forming a hydrophobic mixture by mixing a volatile silicone oil, a non-volatile oil and a wax structurant at an elevated temperature or bringing the mixture to the elevated temperature at which the structurant melts or is dissolved or dispersed in the oils, thereby forming a mobile hydrophobic mixture,
   simultaneously or sequentially forming an aqueous phase comprising water soluble or miscible constituents,
   shear mixing the mobile hydrophobic mixture with the aqueous phase in the presence of an emulsifier, and any insoluble particulate materials thereby forming an emulsion comprising a hydrophobic continuous phase and a disperse aqueous phase,
   cooling or permitting the emulsion to cool to a temperature at which a solid is formed by the structurant structuring the continuous phase,
   wherein
   the continuous phase comprises from 10 to 35% volatile silicone oil, and from
   5 to 15% non-volatile hydrophobic oil,
   the disperse phase comprises from 40 to 75%,
   the antiperspirant or deodorant active comprises from 0.5 to 35%
   the wax structurant comprises from 7 to 25%,
   the emulsifier comprises from 0.1 to 10%,
   the composition optimally comprising up to 5% insoluble particulate materials,
   % s being by weight based on the composition.

30. A method for preventing or reducing perspiration on human skin comprising topically applying to the skin an anhydrous antiperspirant composition comprising an antiperspirant active, a liquid carrier and a structurant which comprises an organic wax having a melting point of from 40 to 90° C. of which at least 60% of the weight of the wax is provided by at least one aliphatic ester satisfying the formula:

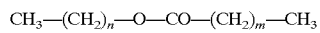

in which n is from 9 to 39 and m is from 0 to 35.

31. A method for preventing or reducing perspiration on human skin comprising topically applying to the skin an antiperspirant composition comprising an antiperspirant active, a liquid carrier and a structurant which comprises an organic wax having a melting point of from 40 to 90° C. of which at least 60% of the weight of the wax is provided by at least one aliphatic ester satisfying the formula:

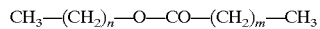

in which n is from 9 to 39 and m is from 0 to 35,
   the antiperspirant composItion being an emulsion in which the continuous phase comprises from 10 to 35% volatile silicone oil, and
   from 5 to 15% non-volatile hydrophobic oil,
   the disperse phase comprises from 40 to 75%,
   the antiperspirant or deodorant active comprises from 0.5 to 35%,
   the wax structurant comprises from 7 to 25%,
   the emulsifier comprises from 0.1 to 10%,
   and the composition preferably contains up to 5% insoluble particulate materials
   % s being by weight.

32. A composition according to claim 12 wherein the disperse phase comprises from 45 to 60%.

33. A composition according to claim 12 containing from 10 to 15% by weight structurant.

34. A composition according to claim 21 wherein the weight ratio of antiperspirant active to non-volatile oil is from 2:1 to 10:3.

35. A composition according to claim 12 further containing from 3 to 12% by weight of a polyhydric alcohol.

* * * * *